US010663438B2

(12) United States Patent
Douglass et al.

(10) Patent No.: US 10,663,438 B2
(45) Date of Patent: May 26, 2020

(54) COMPOUNDS AND METHODS FOR PEG METABOLITE AND PEG BREAKDOWN PRODUCT ASSAYS

(71) Applicant: ColonaryConcepts LLC, Palm Beach Gardens, FL (US)

(72) Inventors: Kevin Douglass, Portage, MI (US); David Humphries, Mattawan, MI (US); Beauregard Mason, Portage, MI (US); Mario Pellerin, Kalamazoo, MI (US)

(73) Assignee: COLONARYCONCEPTS LLC, Palm Beach Gardens, FL (US)

( * ) Notice: Subject to any disclaimer, the term of this patent is extended or adjusted under 35 U.S.C. 154(b) by 109 days.

(21) Appl. No.: 16/054,265

(22) Filed: Aug. 3, 2018

(65) Prior Publication Data

US 2018/0348177 A1  Dec. 6, 2018

Related U.S. Application Data

(63) Continuation of application No. 15/057,989, filed on Mar. 1, 2016, now Pat. No. 10,067,103.

(Continued)

(51) Int. Cl.
*G01N 30/06* (2006.01)
*G01N 33/50* (2006.01)
(Continued)

(52) U.S. Cl.
CPC ......... *G01N 30/7233* (2013.01); *C07C 69/76* (2013.01); *C07C 69/78* (2013.01);
(Continued)

(58) Field of Classification Search
CPC .. C07C 69/76; C07C 69/78; G01N 2030/067; G01N 2560/00; G01N 30/06; G01N 30/7233; G01N 33/50
See application file for complete search history.

(56) References Cited

U.S. PATENT DOCUMENTS 6,048,901 A   4/2000  Cleveland et al.
6,162,464 A   12/2000 Jacob et al.
(Continued)

FOREIGN PATENT DOCUMENTS

CA   2424587 A1   4/2002
CN   101897721 A  12/2010
(Continued)

OTHER PUBLICATIONS

Perala et at. 'Quantitation of Diethylene Glycol and Its Metabolites by Gas Chromatography Mass Spectrometry or Ion Chromatography Mass Spectrometry in Rat and Human Biological Samples', Journal of Analytical Toxicology 2014, vol. 38, pp. 184-193 (Year: 2014).*

(Continued)

*Primary Examiner* — Jennifer Wecker
(74) *Attorney, Agent, or Firm* — Wilson Sonsini Goodrich & Rosati

(57) ABSTRACT

Disclosed herein are compounds and methods for identifying and quantifying a metabolite or breakdown product of PEG. A sample may be assayed for PEG metabolites or breakdown products using liquid chromatography combined with mass spectrometry. Derivatization of the PEG metabolites or breakdown products within the sample with pentaflurobenzoyl chloride in conjunction with negative chemical ionization mode liquid chromatography optimizes the assay.

25 Claims, 7 Drawing Sheets

Related U.S. Application Data

(60) Provisional application No. 62/127,198, filed on Mar. 2, 2015.

(51) Int. Cl.
    *C07C 69/78*     (2006.01)
    *C07C 69/76*     (2006.01)
    *G01N 30/72*     (2006.01)

(52) U.S. Cl.
    CPC .............. *G01N 30/06* (2013.01); *G01N 33/50* (2013.01); *G01N 2030/067* (2013.01); *G01N 2560/00* (2013.01)

(56) References Cited

U.S. PATENT DOCUMENTS

| | | |
|---|---|---|
| 6,444,198 B1 | 9/2002 | Daggy et al. |
| 6,447,763 B1 | 9/2002 | Gordon |
| 6,645,481 B1 | 11/2003 | Cleveland et al. |
| 6,866,873 B2 | 3/2005 | Stern |
| 6,939,563 B2 | 9/2005 | Corpet et al. |
| 6,946,149 B2 | 9/2005 | Cleveland |
| 7,169,381 B2 | 1/2007 | Barras et al. |
| 7,256,202 B2 | 8/2007 | Halow |
| 7,282,223 B2 | 10/2007 | Stern |
| 7,291,324 B2 | 11/2007 | Pelham et al. |
| 7,332,184 B2 | 2/2008 | Vanner et al. |
| 7,495,063 B2 | 2/2009 | Thompson et al. |
| 7,658,914 B2 | 2/2010 | Barras et al. |
| 7,718,197 B2 | 5/2010 | Skiendzielewski et al. |
| 8,057,831 B2 | 11/2011 | Donaldson |
| 8,211,417 B1 | 7/2012 | Snady |
| 8,247,008 B2 | 8/2012 | Donaldson |
| 8,361,452 B2 | 1/2013 | Halow |
| 8,425,944 B2 | 4/2013 | Caswell |
| 8,507,009 B2 | 8/2013 | Skiendzielewski et al. |
| 8,778,306 B2 | 7/2014 | Bachwich |
| 8,829,017 B2 | 9/2014 | Forbes et al. |
| 10,067,103 B2 | 9/2018 | Douglass et al. |
| 2004/0175776 A1 | 9/2004 | Kanai et al. |
| 2005/0037386 A1 | 2/2005 | Morrison et al. |
| 2005/0152989 A1 | 7/2005 | Pelham et al. |
| 2006/0029570 A1 | 2/2006 | Aronson et al. |
| 2007/0232579 A1 | 10/2007 | Freeman et al. |
| 2008/0213393 A1 | 9/2008 | Skiendzielewski et al. |
| 2008/0260682 A1 | 10/2008 | Rose et al. |
| 2009/0324736 A1 | 12/2009 | Johnson et al. |
| 2010/0159026 A1 | 6/2010 | Skiendzielewski et al. |
| 2010/0178360 A1 | 7/2010 | Deviere et al. |
| 2010/0255122 A1 | 10/2010 | Garren et al. |
| 2010/0278949 A1 | 11/2010 | Scott |
| 2011/0065740 A1 | 3/2011 | Forbes et al. |
| 2011/0223252 A1 | 9/2011 | Borody et al. |
| 2011/0229870 A1 | 9/2011 | Seidel |
| 2012/0021064 A1 | 1/2012 | Patton |
| 2012/0107430 A1 | 5/2012 | Scott |
| 2013/0164384 A1 | 6/2013 | Johnson et al. |
| 2013/0189377 A1 | 7/2013 | Cockett et al. |
| 2014/0080906 A1 | 3/2014 | Ervin et al. |
| 2014/0235730 A1 | 8/2014 | Subramanian et al. |
| 2014/0255495 A1 | 9/2014 | Bachwich |
| 2015/0224127 A1 | 8/2015 | Nizam |
| 2016/0258912 A1 | 9/2016 | Douglass et al. |

FOREIGN PATENT DOCUMENTS

| | | |
|---|---|---|
| CN | 102805752 A | 12/2012 |
| EP | 1326592 A1 | 7/2003 |
| EP | 1337264 A1 | 8/2003 |
| EP | 2709641 A1 | 3/2014 |
| JP | 2000088834 | 3/2000 |
| JP | 2006138786 A | 6/2006 |
| JP | 2011529173 A | 12/2011 |
| NZ | 525533 A | 9/2004 |
| WO | WO-0226222 A2 | 4/2002 |
| WO | WO-0230439 A1 | 4/2002 |
| WO | WO-2004006833 A2 | 1/2004 |
| WO | WO-2010081781 A1 | 7/2010 |
| WO | WO-2012158048 A1 | 11/2012 |
| WO | WO-2013044085 A1 | 3/2013 |
| WO | WO-2014032108 A1 | 3/2014 |
| WO | WO-2016140981 A1 | 9/2016 |

OTHER PUBLICATIONS

Gudihal et al. Analysis of Polyethylene Glycol (PEG) and a Mono and Di-PEGylated Therapeutic Protein Using HPLC and Q-TOF Mass Spectrometry, Aligent Technologies, 2012, pp. 1-6 (Year: 2012).*

Dwyer and Tiedje, Metabolism of polyethylene glycol by two anaerobic bacteria, *Desulfovibrio desulfuricans* and a Bacteroids sp Applied and Environmental Microbiology, 52(4): 852-856, 1986.

Gudihai and Babu, Analysis of polyethylene glycol (PEG) and a mono and di-PEGylated therapeutic protein using HPLC and Q-TOF mass spectrometry. Aoolication Note Agilent Technologies, p. 1-6, 2012.

PCT/US2016/020288 International Preliminary Report on Patentability dated Sep. 14, 2017.

PCT/US2016/020288 International Search Report and Written Opinion dated May 17, 2016.

Perala et al., Quantitation of diethylene glycol and its metabolites by gas chromatography mass spectrometry or ion chromatography mass spectrometry in rat and human biological studies Journal of Analytical Toxicology, 38:184-193, 2014.

U.S. Appl. No. 15/057,989 Notice of Allowance dated May 9, 2018.

U.S. Appl. No. 15/057,989 Office Action dated Dec. 5, 2017.

Perala et al.: Quantitation of Diethylene Glycoln and Its Metabolites by Gas Chromatography Mass Spectrometry or Ion Chromatography Mass Spectrometry in Rat and Human Biological Samples; Journal of Analytical Toxicology; 38(4); 184-193 (2014).

Cappiello et al.: LC-ESI-MS determination of diethylene glycol pollution in sea water samples collected around gas extraction platform plants. Talanta 80(1): 257-262 (2009).

Gao et al.: Improvement of Sensitivity for the Determination of Propylene Glycol in Rat Plasma and Lung Tissue Using HPLC/Tandem MS and Derivatization with Benzoyl Chloride. Journal of Liquid Chromatography & Related Technologies 26(20): 3413-3431 (2003).

Imbert et al.: Analysis of eight glycols in serum using LC-ESI-MS-MS. J Anal Toxicol. 38(9): 676-680 (2014).

Pelham et al.: Clinical trial: single- and multiple-dose pharmacokinetics of polyethylene glycol (Peg-3350) in healthy young and elderly subjects. Aliment Pharmacol Ther. 28(2): 256-265 (2008).

Tran et al.: Determination of trace amounts of ethylene glycol and its analogs in water matrixes by liquid chromatography/tandem mass spectrometry. J AOAC Int. 97(1): 232-237 (2014).

* cited by examiner

| [x] / ng/mL | Level | n | Calc [x] | s | % RSD | % Accuracy |
|---|---|---|---|---|---|---|
| 100 | STD 1 | 1 | 103 | N/A | N/A | 102.8 |
| 250 | STD 2 | 2 | 233 | 0.8 | 0.3 | 93.2 |
| 500 | STD 3 | 2 | 516 | 5.9 | 1.1 | 103.1 |
| 750 | STD 4 | 2 | 782 | 4.4 | 0.6 | 104.3 |
| 1000 | STD 5 | 2 | 1018 | 46.3 | 4.6 | 101.8 |
| 2500 | STD 6 | 2 | 2486 | 126.2 | 5.1 | 99.4 |
| 5000 | STD 7 | 2 | 4941 | 83.5 | 1.7 | 98.8 |
| 9000 | STD 8 | 2 | 9094 | 222.5 | 2.4 | 101.0 |
| 10000 | STD 9 | 2 | 9686 | 370.6 | 3.8 | 96.9 |

*FIG. 6*

| [x] / ng/mL | Level | n | Calc [x] | s | % RSD | % Accuracy |
|---|---|---|---|---|---|---|
| 20 | STD 1 | 2 | 18.8 | 0.8 | 4.2 | 94.2 |
| 50 | STD 2 | 2 | 56.3 | 1.6 | 2.9 | 112.6 |
| 100 | STD 3 | 2 | 102 | 6.9 | 6.8 | 102.3 |
| 150 | STD 4 | 2 | 159 | 5.7 | 3.6 | 106.3 |
| 200 | STD 5 | 2 | 196 | 2.9 | 1.5 | 97.8 |
| 500 | STD 6 | 2 | 480 | 14.1 | 2.9 | 96.0 |
| 1000 | STD 7 | 2 | 989 | 34.3 | 3.5 | 98.9 |
| 1800 | STD 8 | 2 | 1753 | 1.8 | 0.1 | 97.4 |
| 2000 | STD 9 | 2 | 1893 | 119.3 | 6.3 | 94.7 |

*FIG. 7*

COMPOUNDS AND METHODS FOR PEG METABOLITE AND PEG BREAKDOWN PRODUCT ASSAYS

CROSS-REFERENCE

This application is a continuation of U.S. patent application Ser. No. 15/057,989, filed Mar. 1, 2016, which claims the benefit of U.S. Provisional Patent Application No. 62/127,198, filed Mar. 2, 2015, which is incorporated herein by reference in its entirety.

BACKGROUND

Polyethylene glycol (PEG) is a polyether that is commonly used as a laxative. For example, PEG may be used to purge the GI tract of an individual in preparation for a medical or surgical procedure.

PEG may break down into its component elements, for example, as a result of the digestive process or for other reasons. Breakdown products of PEG include ethylene glycol and diethylene glycol. The ingestion of PEG or a PEG containing substance by an individual may result in the production of certain PEG metabolites including ethylene glycol and diethylene glycol. Following the ingestion of PEG, PEG metabolites may be present in, for example, the blood, urine, or digestive system of an individual who has ingested PEG.

PEG break down may also occur within a PEG containing product or solution. For example, a PEG containing bowel preparation may contain a certain amount of PEG breakdown products even before the PEG containing product or solution is ingested.

Generally, the metabolites of ingested compounds as well as the breakdown products of compounds may be assayed for in samples. Metabolites may be assayed for in samples taken from subjects who have ingested said compounds. Breakdown products may be assayed for in samples taken from compounds or solutions that contain said breakdown products. Such assays may be used to, for example, determine the presence of and quantity of said metabolites or breakdown products in a sample.

SUMMARY

Provided herein are compounds and methods for detecting and quantifying PEG metabolites and PEG breakdown products with a high degree of sensitivity, accuracy, and reproducibility. Detecting PEG metabolites may be useful in assessing the presence of PEG metabolites within the body of an individual who has ingested PEG. Detecting PEG breakdown products may be useful in assessing the presence of PEG breakdown products before a PEG containing compound or mixture is ingested. Detecting and quantifying a metabolite in a sample taken from an individual may be generally useful to, for example, determine the toxicity of either the substance or its metabolites. Likewise, detecting and quantifying breakdown products of, for example, a substance is useful to, for example, determine the toxicity of the substance and its breakdown products.

Described herein is a method for detecting and quantifying a compound. The method comprises obtaining a sample, wherein the sample contains one or more of ethylene glycol and diethylene glycol. The sample is combined together with aqueous pentaflurobenzoyl chloride in the presence of an aqueous hydroxide containing salt thus producing an aqueous solution, which comprises a pentafluorobenzoate ester derivative. A liquid phase supernatant is separated from the aqueous solution, and the supernatant is analyzed using liquid chromatography and mass spectrometry (LC/MS) to both detect and quantify the pentafluorobenzoate ester derivative that was produced.

The sample obtained from the individual may comprise a specimen taken from an individual who has ingested polyethylene glycol (PEG). The specimen obtained from the individual who has ingested PEG may comprise a tissue sample of a body fluid sample. A tissue or body fluid sample may comprise an organ or a portion thereof, blood, plasma, urine, stool sample, cerebrospinal fluid or other tissue or body fluid.

Pentaflurobenzoyl chloride used in the described method may be dissolved in hexane. The hydroxide containing salt may comprise sodium hydroxide. If the hydroxide salt used is sodium hydroxide, it may comprise a 5M concentration. Alternatively, the hydroxide containing salt may comprise potassium hydroxide.

The aqueous solution of the assay, which comprises the sample obtained from an individual who has ingested PEG may comprise about 100-10,000 ng/ml of ethylene glycol. Ethylene glycol may be quantified at a concentration of about 100 ng/ml of ethylene glycol per sample.

The aqueous solution of the assay, which comprises the sample obtained from an individual who has ingested PEG may comprise about 20-2,000 ng/ml of diethylene glycol. Diethylene glycol may be quantified at a concentration of about 20 ng/ml of ethylene glycol per sample.

The separating step of the assay may comprise centrifuging the aqueous solution, and the assay may further comprise the step of snap freezing said aqueous solution.

The LC/MS mode used may comprise a negative chemical ionization mode.

The pentafluorobenzoate ester derivative product may comprise ethane-1,2-diyl bis(2,3,4,5,6-pentafluorobenzoate), and ethane-1,2-diyl bis(2,3,4,5,6-pentafluorobenzoate) may have a retention time between 0.8 and 1.4 minutes. More specifically, ethane-1,2-diyl bis(2,3,4,5,6-pentafluorobenzoate) may have a retention time of about 1.05 minutes.

The pentafluorobenzoate ester derivative product may comprise 2,2'-oxybis(ethane-2,1-diyl) bis(2,3,4,5,6-pentafluorobenzoate), and 2,2'-oxybis(ethane-2,1-diyl) bis(2,3,4,5,6-pentafluorobenzoate) has a retention time between 0.8 and 1.4 minutes. More specifically, 2,2'-oxybis(ethane-2,1-diyl) bis(2,3,4,5,6-pentafluorobenzoate) may have a retention time of about 0.96 minutes.

Also described herein is a compound comprising ethane-1,2-diyl bis(2,3,4,5,6-pentafluorobenzoate). Ethane-1,2-diyl bis(2,3,4,5,6-pentafluorobenzoate) may have a liquid chromatography retention time between 0.8 and 1.4 minutes. More specifically, ethane-1,2-diyl bis(2,3,4,5,6-pentafluorobenzoate) may have a liquid chromatography retention time of about 1.05 minutes.

Also described herein is a compound comprising ethane-1,2-diyl bis(2,3,4,5,6-pentafluorobenzoate). 2,2'-oxybis(ethane-2,1-diyl) bis(2,3,4,5,6-pentafluorobenzoate) may have a liquid chromatography retention time between 0.8 and 1.4 minutes. More specifically, 2,2'-oxybis(ethane-2,1-diyl) bis(2,3,4,5,6-pentafluorobenzoate) has a liquid chromatography retention time of about 0.96 minutes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the individual matter set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows an exemplary table of calibration data for known quantities of ethylene glycol; and FIG. 7 shows an exemplary table of calibration data for known quantities of diethylene glycol.

DETAILED DESCRIPTION

Figure 1:
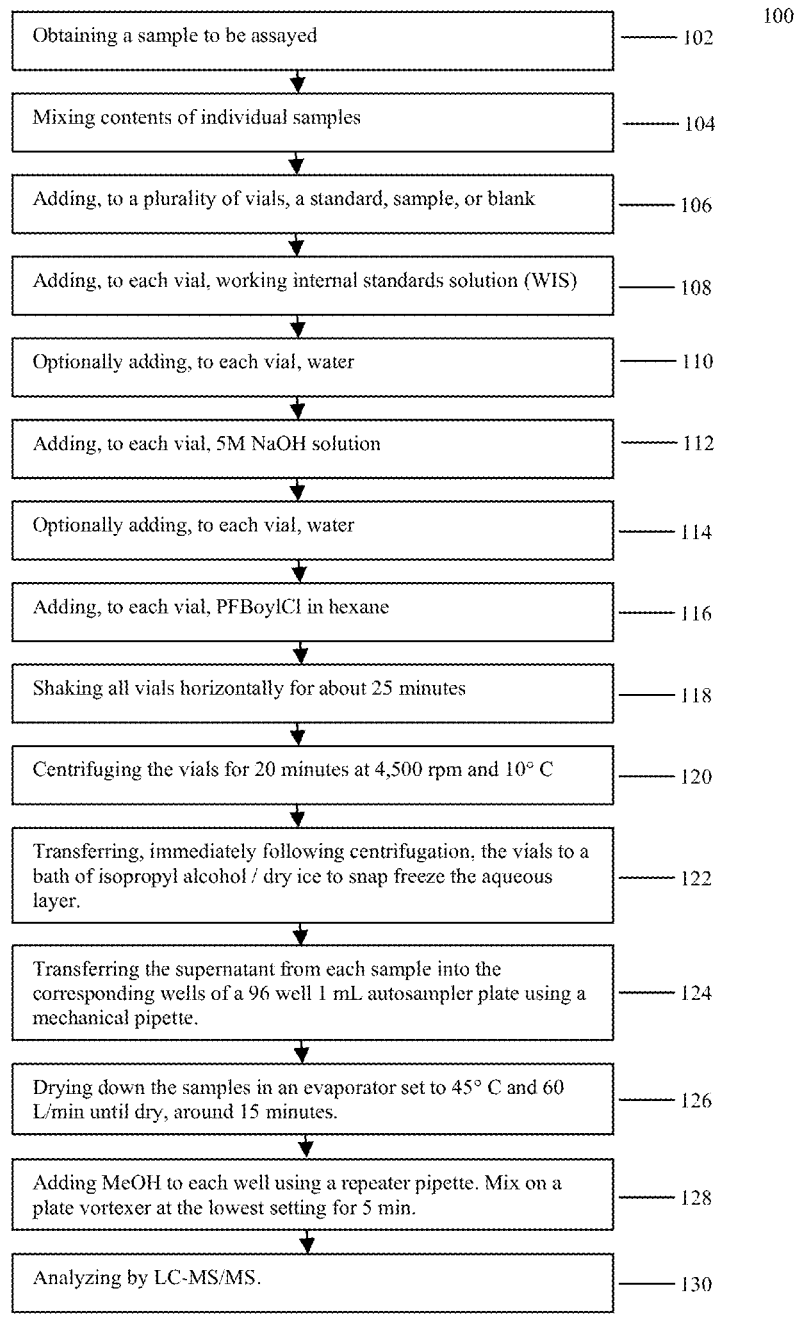
FIG. 1 shows a schematic representation of an exemplary method for accurately detecting and quantifying PEG metabolites or PEG breakdown products within a sample.

Before describing the individual matter disclosed herein in detail, it is to be understood that the individual matter is not limited in its application to the details of construction, experiments, exemplary data, and/or the arrangement of the components set forth in the following description, or illustrated in the drawings. The subject matter described herein is capable of other variations, and therefore the variations described herein should not be taken to limit the scope of the individual matter of the description in any way. Also, it is to be understood that the phraseology and terminology employed herein is for the purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein the term "subject" may comprise a human or any animal species.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Described herein are assays and compounds for detecting, identifying, and quantifying PEG metabolites in a tissue or body fluid sample of an individual as well as PEG breakdown products that may exist in a PEG containing product or solution before the product or solution is ingested.

PEG metabolites are metabolic products of PEG that may be absorbed through the digestive system of an individual who ingests PEG. Generally, once a metabolite is absorbed through the digestive system, the metabolite may, for example, be circulated throughout the body or concentrated in a particular organ. The assays and compounds described herein may be used to detect and quantify PEG metabolites within a tissue or body fluid sample of an individual who has ingested PEG in order, for example, to study the distribution of absorbed PEG metabolites in an individual who has ingested PEG.

PEG breakdown products are chemicals and compounds that result from PEG. Such breakdown products may occur, for example, as a result of degradation of PEG. For example, a therapeutic agent comprising of a PEG compound may comprise breakdown products of PEG as well. These breakdown products may exist while a PEG containing therapeutic agent is, for example, on a shelf in a pharmacy.

PEG is a polymer of ethylene oxide having the general structure $H-(O-CH_2-CH_2)_n-OH$. PEG variants structurally differ from one another by the number "n" of ethylene oxide molecules contained therein. As the number "n" of ethylene oxide units increases, the molecular weight of the PEG molecule increases.

PEG variants are often designated along with a number that represents their average molecular weight. For example, PEG 3350, denotes a PEG compound with an average molecular weight of 3350 Daltons.

Different PEG compounds, having different molecular weights, are used in various applications, including medical and commercial applications. PEG 3350, for example, is used as the active pharmaceutical ingredient in a number of orally and rectally administered laxatives. PEG 3350 is also the active pharmaceutical ingredient in bowel preparation formulations used to wash or irrigate the bowel in preparation for a number of medical and surgical procedures including colonoscopy.

The mechanism of action of PEG 3350 is an osmotic drawing of fluid into the GI tract of the individual. The increased fluid in the GI tract that is drawn into the GI tract by the actions of PEG is retained in the stool of the individual, thus softening the individual's stool. The increased amount of fluid in the GI tract of the individual also effectively cleanses the GI tract.

PEG, ingested orally by an individual, is typically broken down in the digestive tract into metabolites that may be absorbed and thus found in the tissue or body fluids of the individual. Detecting and quantifying the PEG metabolites found in the tissue or body fluids of an individual provides information regarding PEG's distribution throughout the body of the individual beyond its targeted site of activity (i.e. the GI tract).

Likewise, an assay that detects and quantifies PEG breakdown products in a product or solution containing PEG provides information regarding potentially toxic PEG breakdown products in that PEG containing product or solution. For example a therapeutic agent containing PEG or a food containing PEG may contain a quantity of PEG breakdown products that may be detected and quantified using an assay.

A non-limiting list of examples of PEG metabolites may include ethylene glycol, diethylene glycol, glycolic acid, and diglycolic acid. These PEG metabolites may be found in, for example, the blood or GI system of an individual who has ingested PEG, wherein the GI system may comprise all organs of the GI system as well as GI products such as, for example, bile, digestive enzymes, and stool. PEG metabolites may further be found in, for example, any tissue or body fluid of an individual including, for example, all organs, blood, plasma, lymph, saliva, cerebrospinal fluid, urine, and sweat.

A non-limiting list of examples of PEG breakdown products may include ethylene glycol, diethylene glycol, glycolic acid, and diglycolic acid. These breakdown products may be found in PEG containing compounds and mixtures. For example, PEG breakdown products may be assayed for in a sample comprising a therapeutic compound which comprises PEG. For example, PEG breakdown products may be assayed for in a sample substantially comprising only PEG. For example, PEG breakdown products may be assayed for in a sample comprising a food mixed together with PEG or a food prepared by mixing together the ingredients that comprise the food together with PEG.

The tissue or body fluid of an individual who has ingested PEG may be sampled by, for example, obtaining a blood sample from said subject. The tissue of an individual may, for example, be sampled by obtaining an organ specimen from said subject, which may comprise, for example, an entire organ or a biopsy. The body fluid of an individual who has ingested PEG may be sampled by, for example, obtaining a bile sample, urine sample, or other body fluid sample from said subject.

Once obtained, the tissue or body fluid sample may be analyzed in different ways using the analysis methods and compounds described herein. For example, the PEG metabolite ethylene glycol may be both detected and quantified within a blood sample of an individual who has ingested PEG with a high degree of sensitivity, accuracy, and reproducibility using the analysis methods and compounds described herein.

When sampling for breakdown products in products containing PEG samples may be obtained by, for example, dissolving the PEG containing compound in a suitable solvent. The PEG containing compound may be first pulverized or reduced in size by other means as well including crushing and grinding of the PEG containing compound.

In some embodiments the methods described herein involve the following steps. A tissue or fluid sample (or multiple tissue or body fluid samples) is collected from an individual who has ingested PEG. PEG metabolites may be extracted from the sample. The sample or extracted metabolites are then reacted with a derivatizing agent to form a product compound that comprises both a PEG metabolite and the derivatizing agent. The product compound is then separated from the sample by, for example, centrifuging the sample to generate a supernatant layer comprising the newly formed compound comprising the derivatizing agent bound to a PEG metabolite. The supernatant is separated, placed in a tray, and passed through a liquid chromatography column and mass spectrometer (i.e. LC/MS) to generate a 2D chromatogram. The 2D chromatogram gives a readout with a fairly predictable retention time for each of the respective PEG metabolites. Calibration data comprising readouts for known quantities of PEG metabolites are generated. The responses of the calibration samples are plotted against their respective concentrations and the points are then fit with an equation that can be used to determine an unknown sample's concentration if its response is known. The calibration data is then used to quantify unknown metabolite quantities in the various samples obtained from subjects who ingested PEG.

In some embodiments the methods described herein involve the following steps. A sample of PEG containing compound (e.g. a PEG containing therapeutic product) is obtained. The PEG breakdown products may be extracted from the sample. The sample or the extracted PEG breakdown products may then be reacted with a derivatizing agent to form a product compound that comprises both a PEG breakdown product and the derivatizing agent. The product compound is then separated from the sample by, for example, centrifuging the sample to generate a supernatant layer comprising the newly formed compound comprising the derivatizing agent bound to a PEG metabolite. The supernatant is separated, placed in a tray, and passed through a liquid chromatography column and mass spectrometer (i.e. LC/MS) to generate a 2D chromatogram. The 2D chromatogram gives a readout with a fairly predictable retention time for each of the respective PEG metabolites. Calibration data comprising readouts for known quantities of PEG metabolites are generated. The responses of the calibration samples are plotted against their respective concentrations and the points are then fit with an equation that can be used to determine an unknown sample's concentration if its response is known. The calibration data is then used to quantify unknown metabolite quantities in the various samples obtained from subjects who ingested PEG.

As stated, a 2D LC/MS chromatogram may comprise the retention time (using chromatography) and intensity of a substance (using mass spectroscopy. The time that it takes for a sample to pass through the chromatography column is generally known as the retention time of that sub stance.

The retention time of the same substance may vary significantly from column to column depending at least in part on the properties of the column and conditions used for running the substance through the column.

Retention time is typically measured on the x-axis of a 2D LC/MS chromatogram. The retention time of a substance may be determined at least in part by the polarity of the substance. The retention time of a substance on an LC column is generally shorter than one obtained by other common chromatographic methods such as gas chromatography (GC).

The intensity of the substance on mass spectrometry may be determined at least in part by the ionization efficiency of the substance.

Intensity is typically measured on the y-axis of a 2D LC/MS chromatogram. Ionization methods common for LC/MS, such as electrospray ionization (ESI), result in intact molecules of the substance, as opposed to high-energy ionization methods used in GC which result in extensive fragmentation of the substance.

Generally, the PEG metabolite and PEG breakdown product containing samples may comprise multiple other substances that have mass-to-charge ratios and polarities similar to those of PEG metabolites and PEG breakdown products thus making it difficult to separate a substance to be analyzed from other substances contained in tissue samples on a chromatogram that is produced. That is, substances having similar polarities and mass-to-charge ratios will cluster around the same section of the 2D chromatogram creating background noise that may make it difficult to identify the substance of interest from the background noise created by the other substances. Background noise on LC/MS is an issue when analyzing PEG metabolites in tissue or body fluid samples.

Substances can be separated from background noise on LC/MS by, for example, binding the substances to a derivatizing agent, thus creating a new compound (comprising of the substance bound to the derivatizing agent) that has a different retention time or intensity than the substance would alone. For example, chemically modifying a substance of interest being analyzed by reacting it with a derivatizing reagent may affect the polarity of the chemically-modified substance thus affecting the retention time of the substance. For example, the reaction of a substance of interest with a derivatizing reagent may also affect the mass of the chemically-modified substance thus affecting the measured mass-to-charge ratio and intensity of the substance on mass spectroscopy. That is, a product of a derivatizing agent and a substance of interest should have properties that differ from the substance of interest by itself so that a product of the derivatizing agent and substance of interest may have an appearance on 2D chromatography that is removed from the background noise created by the presence of other substances within the sample. That is, the product of a derivatizing agent and a substance of interest may be detectable and quantifiable with a higher sensitivity than the substance alone on certain analytical platforms.

A chemical product of a derivatizing agent with a PEG metabolite, such as ethylene glycol and diethylene glycol, makes LC/MS of PEG metabolites and PEG breakdown products more sensitive and reproducible. The binding of the metabolite or breakdown product to the derivatizing agent makes LC/MS more sensitive and reproducible, because the chemical modification of the metabolite at least separates the metabolites from the background noise created by the other substances within a specimen. For example, a reaction between either ethylene glycol or diethylene glycol with a derivatizing reagent forms a product with a higher retention time than the substance alone, so that the product may appear on the chromatogram at a position further along the x-axis than the PEG metabolites would normally appear alone. Likewise, a reaction between either ethylene glycol or diethylene glycol with a derivatizing reagent forms a product with a higher intensity on mass spectrometry so that the product appears further along the y-axis than the PEG metabolites would normally appear alone.

Pentaflurobenzoyl chloride is a molecule that reacts with PEG metabolites and PEG breakdown products in the presence of NaOH to generate pentafluorobenzoate ester derivatives. Typically, two pentaflurobenzoyl chloride molecules react with either a single ethylene glycol molecule or a single diethylene glycol molecule. Pentafluorobenzoyl chloride contains numerous fluorine atoms, which makes the high fluoride containing product of two pentafluorobenzoyl chloride molecules and a single PEG metabolite or PEG breakdown product optimal for use with negative-mode chemical ionization (NCI) liquid chromatography. NCI is an effective ionization method for substances with a high electron capture efficiency, and because of the high electronegativity of halogen atoms, compounds containing halogen atoms may possess a high electron capture efficiency. NCI is thus effective at optimizing the sensitivity of the PEG metabolite and PEG breakdown product assay due to the presence of fluorine in the reaction products of the PEG metabolites or PEG breakdown products and pentafluorobenzoyl chloride.

The assay methods described herein also involve generating calibration data for known quantities of PEG metabolites or PEG breakdown products. For example, LC/MS calibration data may be collected for 100 ng/ml of ethylene glycol, 250 ng/ml of ethylene glycol, 500 ng/ml of ethylene glycol, and so on until sufficient calibration data is gathered. When a specimen comprising an unknown amount of PEG metabolite or PEG breakdown product ethylene glycol is run through LC/MS, a comparison to the calibration values of known quantities of ethylene glycol will allow for extrapolation of the quantity of ethylene glycol present in the sample.

The methods and compounds described herein provide means for detecting and quantifying PEG metabolites and PEG breakdown products with a high degree of sensitivity, accuracy, and reproducibility. Ethylene glycol may, for example, be detected and quantified accurately within a sample in amounts as low as about 100 ng/ml and diethylene glycol may, for example, be detected and quantified accurately within a sample in amounts as low as about 20 ng/ml.

FIG. 1 shows a schematic representation of an exemplary method 100 for accurately detecting and quantifying PEG metabolites and PEG breakdown products within a sample. In a step 102, a sample is obtained from an individual. Alternatively, in step 102, a sample may be obtained from a PEG containing compound. A subject may comprise both a human and an animal subject. A wide variety of sample types are suitable for use with the described method include subject tissue and body fluid specimen. Preferably, blood specimens may be analyzed as the concentration of PEG metabolites in the blood may generally indicate the degree of systemic distribution of PEG metabolites in an individual. However, for example, assays for PEG metabolites within other sample types such as cerebral spinal fluid (CSF) may reflect CNS exposure or bile may reflect the hepatic load of PEG metabolites. Assays for PEG metabolites within, for example, urine may also generally reflect the amount of PEG metabolized. Samples may be obtained directly from an individual, or samples may have been previously frozen. Samples of PEG containing compounds may comprises compounds that are substantially PEG, compounds wherein PEG is bound to another compound or excipient, or compounds wherein PEG is mixed together with other substances. If samples were previously frozen, step 102 will also include thawing said frozen samples at ambient temperature.

In a step 104, the samples are mixed, by for example, a vortex so that the components of the sample will be evenly distributed throughout the sample.

In a step 106, the samples may be transferred to a vial, tube, or other similar container. In addition, standard samples, and blank are added to respective tubes as well. Thus, each assay may include a plurality of vials. The plurality of vials may respectively contain different samples, standard samples, and blank.

In a step 108, working internal standards are added to all of the vials used in the assay.

In a step 110, water is optionally added in equal measure to each of the plurality of vials. The amount of water added may comprise, for example, 150 µL.

In a step 112, a hydroxide containing salt is added to each of the plurality of the vials used in the assay. Non-limiting examples of hydroxide containing salts suitable for use in the assay described herein include sodium hydroxide and potassium hydroxide. The salt hydroxide containing salt is preferably already in solution when added to the plurality of vials used in the assay. If using sodium hydroxide a solution of about 5M NaOH is preferred, but other molarities are suitable as will be understood by one having skill in the art. The amount of 5M NaOH added to each of the plurality of vials may comprise, for example, about 200 µL.

In a step 114, water is optionally added in equal volume to each of the plurality of vials. The amount of water added may comprise, for example, a volume of water that will lower the molarity of a hydroxide containing salt added to the plurality of vials.

In a step 116, a derivatizing agent is added to the plurality of vials. Preferably, the derivatizing agent pentafluorobenzoyl chloride is used. Pentafluorobenzoyl chloride may be dissolved in hexane, but other solvents are suitable as will be understood by those having knowledge in the art. Preferably 1.00 ml of 4% pentafluorobenzoyl chloride in hexane is added to each of the plurality of vials used in the assay. The combination of the organic solvent (containing pentafluorobenzoyl chloride) with an aqueous solvent creates a biphasic liquid system comprising two immiscible liquid phases. It will be understood by those having knowledge in the art that the assays and methods described herein need not be limited to biphasic liquid systems only and that other multiphasic liquid systems are suitable for use as well.

In a step 118, the plurality of vials used in the assay are shaken, preferably with a horizontal shaker. The horizontal shaker is preferably set to the lowest setting to achieve a gentle shaking of the contents of the plurality of the vials.

In a step 120, the plurality of vials are centrifuged. Preferred settings are 4,500 rpm, for 20 minutes at 10 degrees Celsius. Centrifugation produces a supernatant in the vials that contain samples obtained from an individual or multiple subjects. The supernatant that is formed may comprise a compound comprising the derivatizing agent and a PEG metabolite or PEG breakdown products. For example, when pentafluorobenzoyl chloride is used as the derivatizing agent, the supernatant comprises a pentafluorobenzoate ester derivative.

In a step 122, the plurality of vials may be placed in a cold bath, such as a dry ice bath, immediately following centrifugation to snap freeze the aqueous layer.

In a step 124, the supernatant from each vial is transferred to an autosampler plate. A suitable autosampler plate may comprise, for example, a 96 well 1 mL autosampler plate.

In a step 126, the samples in the autosampler plate may be dried by placing the autosampler plate in an evaporator set to, for example 45 degrees Celsius and 60 L/min until the samples are dry.

In a step 128, MeOH may be added to each well, and the autosampler plate may be vortexed on a plate vortexer.

In a step 130, the samples, along with standards, and blank are analyzed using LC-MS/MS.

Figure 2:
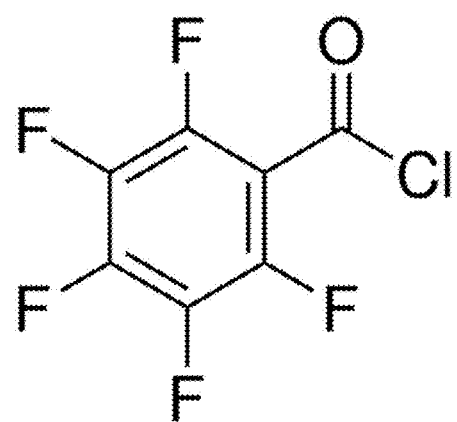
FIG. 2 shows the chemical structure of the derivatizing agent pentafluorobenzoyl chloride.

FIG. 2 shows the chemical structure of the derivatizing agent pentafluorobenzoyl chloride. Generally, derivatization is a technique used in chemistry which transforms a chemical compound into a product (the reaction's derivate) of similar chemical structure, called a derivative. The derivative may have different chemical properties than the non-derivatized chemical compound. Derivatization may, for example, effect melting or boiling points, solubility, or reactivity of a chemical compound.

Bioanalytical assays for ethylene glycol (EG) and diethylene glycol (DEG) alone using a traditional GC-MS/MS approach do not have the required sensitivity by electron ionization. In addition, low molecular weights of the observed fragments will likely make analysis by multiple reaction monitoring (MRM) a challenge.

The PEG metabolites or breakdown products were derivatized with pentafluorobenzoyl chloride to, at least in part, facilitate analysis with LC/MS using negative-mode chemical ionization (NCI). Pentafluorobenzoyl chloride contains numerous Fluorine atoms, and Fluorine is a halogen. Because of the high electronegativity of halogen atoms, halogen containing compounds are particularly suitable for analysis with NCI.

Figure 3:
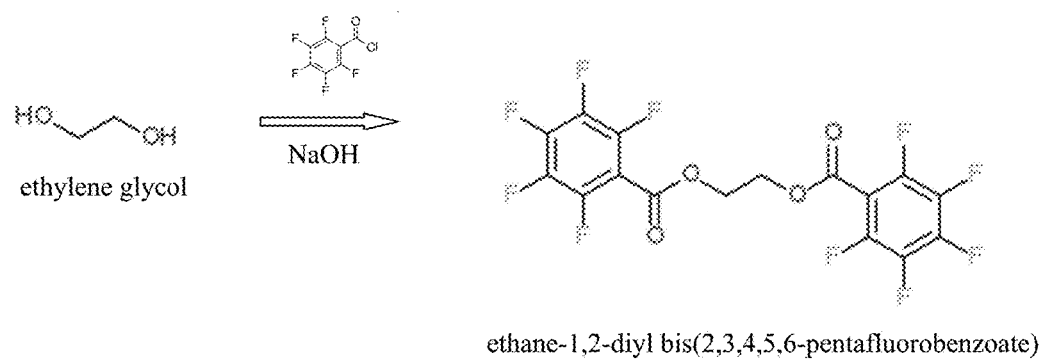
FIG. 3 shows a schematic representation of a chemical process that produces a derivation product ethane-1,2-diyl bis(2,3,4,5,6-pentafluorobenzoate)
Figure 3A:
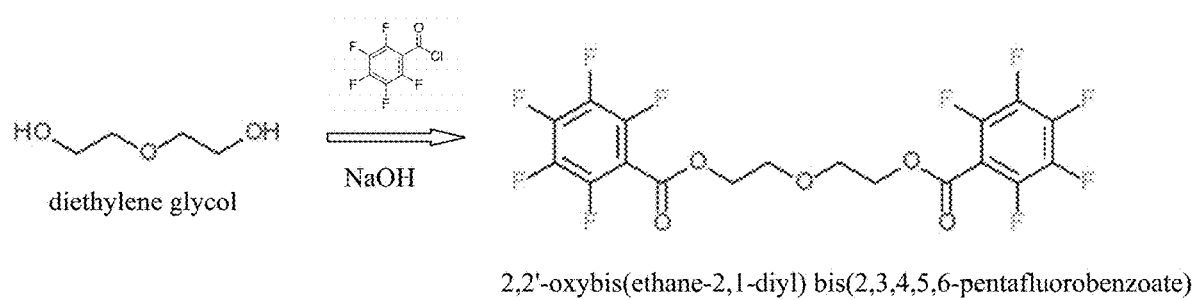
FIG. 3A shows a schematic representation of a chemical process that produces a derivation product 2,2'-oxybis(ethane-2,1-diyl) bis(2,3,4,5,6-pentafluorobenzoate)

FIGS. 3 and 3A show a representation of the chemical reactions that generate the derivatized products of the respective PEG metabolites or breakdown products. As shown in FIG. 3, when ethylene glycol is mixed with pentafluorobenzoyl chloride in the presence of NaOH, the reaction produces a derivation product ethane-1,2-diylbis(2,3,4,5,6-pentafluorobenzoate) comprising two pentafluorobenzoyl chloride molecules bound to a single ethylene glycol molecule. As shown in FIG. 3A, when diethylene glycol is mixed with pentafluorobenzoyl chloride in the presence of NaOH, the reaction produces a derivation product 2,2'-oxybis(ethane-2,1-diyl) bis(2,3,4,5,6-pentafluorobenzoate) comprising two pentafluorobenzoyl chloride molecules bound to a single diethylene glycol molecule.

Figure 4:
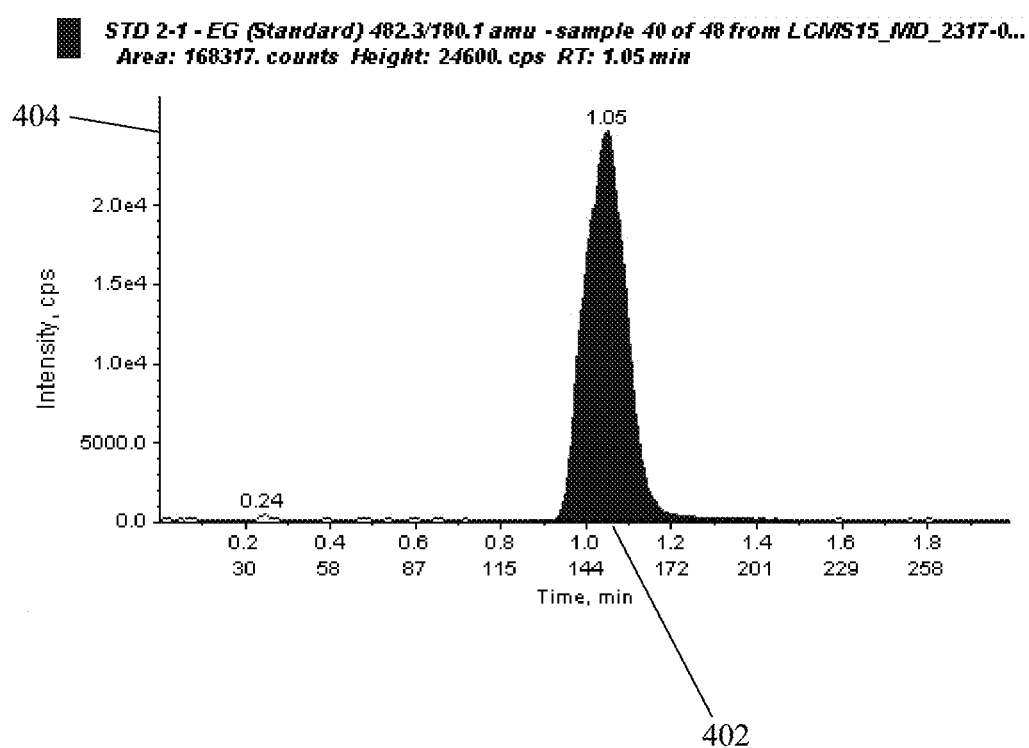
FIG. 4 shows an example of a chromatogram of the derivatization product ethane-1,2-diyl bis(2,3,4,5,6-pentafluorobenzoate)

FIG. 4 shows an example of a chromatogram of the derivatization product ethane-1,2-diyl bis(2,3,4,5,6-pentafluorobenzoate) which was generated from a known starting concentration of ethylene glycol comprising 100 ng/ml. The point along the x-axis corresponding to the apex of the chromatogram curve is the retention time of ethane-1,2-diyl bis(2,3,4,5,6-pentafluorobenzoate) 402. In the example of FIG. 4, the retention time of ethane-1,2-diyl bis(2,3,4,5,6-pentafluorobenzoate) is approximately 1.05 minutes. The point along the y-axis corresponding to the apex of the chromatogram curve is the intensity of ethane-1,2-diyl bis(2,3,4,5,6-pentafluorobenzoate) 402. In the example of FIG. 4, the intensity of ethane-1,2-diyl bis(2,3,4,5,6-pentafluorobenzoate) is approximately 24600 CPS.

Figure 5:
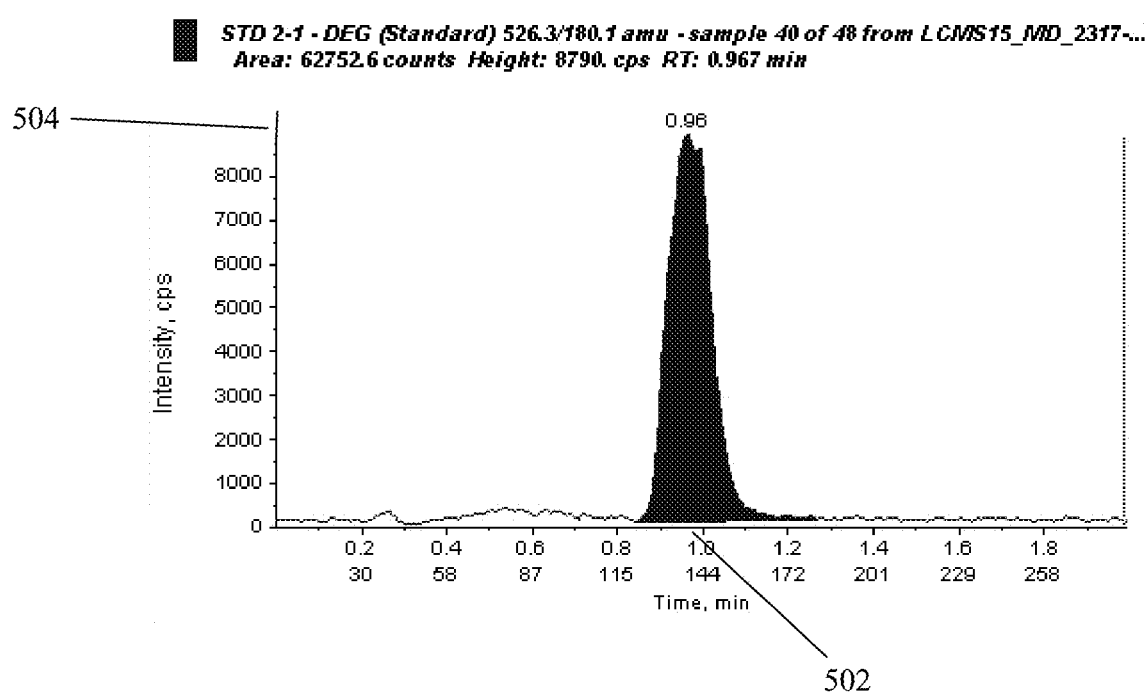
FIG. 5 shows an example of a chromatogram of the derivatization product 2,2'-oxybis(ethane-2,1-diyl) bis(2,3,4,5,6-pentafluorobenzoate)

FIG. 5 shows an example of a chromatogram of the derivatization product 2,2'-oxybis(ethane-2,1-diyl) bis(2,3,4,5,6-pentafluorobenzoate) which was generated from a known starting concentration of diethylene glycol comprising 20 ng/ml. The point along the x-axis corresponding to the apex of the chromatogram curve is the retention time of 2,2'-oxybis(ethane-2,1-diyl) bis(2,3,4,5,6-pentafluorobenzoate) 502. In the example of FIG. 4, the retention time of 2,2'-oxybis(ethane-2,1-diyl) bis(2,3,4,5,6-pentafluorobenzoate) is approximately 0.96 minutes. The point along the y-axis corresponding to the apex of the chromatogram curve is the intensity of 2,2'-oxybis(ethane-2,1-diyl) bis(2,3,4,5,6-pentafluorobenzoate) 504. In the example of FIG. 5, the intensity of ethane-1,2-diyl bis(2,3,4,5,6-pentafluorobenzoate) is approximately 8790 CPS.

FIG. 6 shows an exemplary table of calibration data for known quantities of ethylene glycol. Calibration data is used at least in part to quantify the amount of ethylene glycol within a sample obtained from an individual who has ingested PEG. The sensitivity of the assay described herein is typically most optimal for quantifying an amount of ethylene glycol within the range of about 100-10,000 ng/ml of ethylene glycol.

FIG. 7 shows an exemplary table of calibration data for known quantities of diethylene glycol. Calibration data is used at least in part to quantify the amount of diethylene glycol within a sample obtained from an individual who has ingested PEG. The sensitivity of the assay described herein is typically most optimal for quantifying an amount of ethylene glycol within the range of about 20-2,000 ng/ml of diethylene glycol.

Further details are illustrated by the following non-limiting Examples section.

EXAMPLES

A study was completed, the objective of which was to compare the rate of absorption and oral bioavailability of PEG 3350 along with quantification of PEG metabolites in a test formulation in comparison to the commercially available reference product. The compositions and methods as described herein were used to assay for the PEG metabolites diethylene glycol and ethylene glycol in the study.

A total of 14 subjects were enrolled in this study, and of 12 (85.7%) of those subjects completed the study. This was an open-label, randomized, sequenced, two-period, two-treatment crossover study in which 12 healthy adult subjects were to receive the test formulation in one period and a separate dose of the commercially available product in another period.

Subjects were administered 5 doses of Treatment A, the test formulation, over 14 hours in one period and a single dose of Treatment B, the commercially available product, administered over 3 hours in one period. Both treatments were administered in a randomized, sequenced fashion.

Blood samples were obtained from the test subjects and assayed to determine the pharmacokinetic profile and exposure of PEG 3350 and the following possible PEG 3350 metabolites after each treatment: ethylene glycol (EG) and diethylene glycol (DEG).

Diethylene Glycol (DEG)

In most samples, plasma concentrations of DEG were below the limit of quantitation (BLQ, <40.0 ng/mL). Quantifiable concentrations of DEG were observed for only 3 subjects after the administration of the test formulation: Subject 1903 (2 samples), Subject 1905 (3 samples), and Subject 1916 (3 samples); these concentrations were slightly above the lower limit of quantification (LLOQ) and ranged from 40.9 to 47.5 ng/mL. All other plasma concentrations of DEG for the other nine subjects dosed with ECP and the 12 subjects dosed with the commercially available product were BLQ. Due to these limited quantifiable data, DEG was not included in the pharmacokinetic analysis. Therefore, these data provide no evidence that the PEG 3350 in either the commercially available product or ECP is significantly metabolized to DEG.

Ethylene Glycol (EG)

The mean baseline concentrations of ethylene glycol were 602 ng/mL and 615 ng/mL following ECP Colon Prep Kit and the commercially available product, respectively. Quantifiable concentrations EG were found in every plasma sample prior to and after the administration of both Treatment A, the test formulation, and Treatment B, the commercially available product. The EG levels observed in the study subjects did not change above baseline (zero-time) values over the entire sampling schedule.

The mean EG concentrations observed in the 12 subjects of this study are shown in Table 1.

TABLE 1

| Time (h) | Treatment A: Test Formulation | | | | Treatment B: Reference Product | | | |
|---|---|---|---|---|---|---|---|---|
| | n | Mean (ng/mL) | SD (ng/mL) | CV % | n | Mean (ng/mL) | SD (ng/mL) | CV % |
| 0.00 | 12 | 602 | 60.7 | 10.08 | 12 | 615 | 54.7 | 8.90 |
| 0.50 | 12 | 600 | 39.1 | 6.52 | — | — | — | — |
| 1.00 | 12 | 616 | 32.0 | 5.20 | 12 | 618 | 44.2 | 7.15 |
| 2.00 | 12 | 627 | 55.9 | 8.92 | 12 | 631 | 63.1 | 10.00 |
| 3.00 | 12 | 603 | 50.5 | 8.37 | 12 | 607 | 47.1 | 7.77 |
| 3.50 | 12 | 631 | 52.0 | 8.24 | — | — | — | — |
| 4.00 | — | — | — | — | 12 | 616 | 38.2 | 6.20 |
| 4.50 | 12 | 609 | 42.1 | 6.91 | — | — | — | — |
| 5.00 | 12 | 620 | 44.8 | 7.23 | 12 | 612 | 54.2 | 8.86 |
| 5.50 | 12 | 668 | 75.6 | 11.32 | — | — | — | — |
| 6.00 | 12 | 624 | 45.0 | 7.20 | — | — | — | — |
| 7.00 | — | — | — | — | 12 | 571 | 54.4 | 9.54 |
| 8.00 | 12 | 617 | 47.9 | 7.76 | — | — | — | — |
| 9.00 | — | — | — | — | 12 | 601 | 39.9 | 6.64 |
| 11.00 | 12 | 613 | 37.8 | 6.17 | 12 | 596 | 36.8 | 6.17 |
| 11.50 | 12 | 636 | 52.3 | 8.22 | — | — | — | — |
| 12.50 | 12 | 623 | 40.1 | 6.43 | — | — | — | — |
| 13.50 | 12 | 586 | 60.5 | 10.32 | — | — | — | — |
| 15.00 | — | — | — | — | 12 | 594 | 30.3 | 5.10 |
| 15.50 | 12 | 582 | 48.1 | 8.25 | — | — | — | — |
| 17.50 | 12 | 594 | 43.7 | 7.37 | — | — | — | — |
| 19.50 | 12 | 603 | 57.3 | 9.50 | — | — | — | — |
| 21.00 | — | — | — | — | 12 | 626 | 116 | 18.56 |
| 23.50 | 12 | 589 | 61.5 | 10.44 | — | — | — | — |
| 27.00 | — | — | — | — | 12 | 596 | 24.2 | 4.05 |
| 29.50 | 12 | 587 | 49.6 | 8.45 | — | — | — | — |
| 35.50 | 12 | 584 | 39.4 | 6.74 | — | — | — | — |
| 39.00 | — | — | — | — | 12 | 594 | 28.2 | 4.74 |
| 47.50 | 12 | 590 | 32.7 | 5.54 | — | — | — | — |
| 51.00 | — | — | — | — | 12 | 583 | 39.6 | 6.78 |
| 59.50 | 12 | 583 | 39.9 | 6.84 | — | — | — | — |

While preferred embodiments of the present individual matter have been shown and described herein, it will be obvious to those skilled in the art that such embodiments are provided by way of example only. Numerous variations, changes, and substitutions will now occur to those skilled in the art without departing from the individual matter. It should be understood that various alternatives to the embodiments of the individual matter described herein may be employed in practicing the individual matter described herein. It is intended that the following claims define the scope of the individual matter described herein and that methods and structures within the scope of these claims and their equivalents be covered thereby.

What is claimed is:

1. A method for detecting and quantifying a compound, said method comprising
    obtaining a sample, said sample containing one or more of ethylene glycol and diethylene glycol;
    combining said sample, an aqueous hydroxide containing salt, and pentaflurobenzoyl chloride dissolved in an organic solvent thus producing a biphasic liquid system, said biphasic liquid system comprising a pentafluorobenzoate ester derivative;
    separating a liquid phase supernatant from said biphasic liquid system; and
    analyzing said supernatant using liquid chromatography and mass spectrometry (LC/MS) to detect a retention time of said pentafluorobenzoate ester derivative;
    wherein ethylene glycol in said sample is quantified based on said retention time of said pentafluorobenzoate ester derivative; and
    wherein diethylene glycol is quantified based on said retention time of said pentafluorobenzoate ester derivative.

2. The method of claim 1, wherein said sample comprises a specimen taken from an individual who has ingested polyethylene glycol (PEG).

3. The method of claim 2, wherein said specimen comprises a blood specimen.

4. The method of claim 2, wherein said specimen comprises a urine specimen.

5. The method of claim 2, wherein said specimen comprises a bile specimen.

6. The method of claim 2, wherein said specimen comprises an organ specimen.

7. The method of claim 2, wherein said specimen comprises a cerebrospinal fluid specimen.

8. The method of claim 1, wherein said sample comprises PEG or a PEG containing compound.

9. The method of claim 8, wherein said PEG containing compound is a mixture of PEG and another compound.

10. The method of claim 1, wherein said pentaflurobenzoyl chloride is dissolved in hexane.

11. The method of claim 1, wherein said hydroxide containing salt comprises sodium hydroxide.

12. The method of claim 11, wherein said sodium hydroxide comprises a 5M sodium hydroxide solution.

13. The method of claim 1, wherein said hydroxide containing salt comprises potassium hydroxide.

14. The method of claim 1, wherein said biphasic liquid system comprises about 100-10,000 ng/ml of ethylene glycol.

15. The method of claim 1, comprising quantifying said pentafluorobenzoate ester derivative.

16. The method of claim 15, wherein said ethylene glycol is quantified based on said pentafluorobenzoate ester derivative at a concentration of about 100 ng/ml of ethylene glycol per sample.

17. The method of claim 15, wherein said diethylene glycol is quantified based on said pentafluorobenzoate ester derivative at a concentration of about 20 ng/ml of diethylene glycol per sample.

18. The method of claim 1, wherein said biphasic liquid system comprises about 20-2,000 ng/ml of diethylene glycol.

19. The method of claim 1, wherein said separating step comprises centrifuging said biphasic liquid system.

20. The method of claim 1, further comprising the step of snap freezing said biphasic liquid system.

21. The method of claim 1, wherein said LC/MS comprises a negative chemical ionization mode.

22. The method of claim 1, wherein said pentafluorobenzoate ester derivative comprises ethane-1,2-diyl bis(2,3,4,5,6-pentafluorobenzoate).

23. The method of claim 22, wherein ethane-1,2-diyl bis(2,3,4,5,6-pentafluorobenzoate) has a retention time that is greater than a retention time of ethylene glycol.

24. The method of claim 1, wherein said pentafluorobenzoate ester derivative comprises 2,2'-oxybis(ethane-2,1-diyl) bis(2,3,4,5,6-pentafluorobenzoate).

25. The method of claim 24, wherein 2,2'-oxybis(ethane-2,1-diyl) bis(2,3,4,5,6-pentafluorobenzoate) has a retention time that is greater than a retention time of diethylene glycol.

\* \* \* \* \*